(12) United States Patent
Lin et al.

(10) Patent No.: US 12,416,036 B2
(45) Date of Patent: Sep. 16, 2025

(54) HIGH-THROUGHPUT ENZYME ASSAY FOR SCREENING ACTIVITY OF ACYLTRANSFERASES

(71) Applicant: CORNELL UNIVERSITY, Ithaca, NY (US)

(72) Inventors: Hening Lin, Ithaca, NY (US); Maurine E. Linder, Ithaca, NY (US); Jun Young Hong, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/840,140

(22) Filed: Jun. 14, 2022

(65) Prior Publication Data

US 2022/0403443 A1 Dec. 22, 2022

Related U.S. Application Data

(60) Provisional application No. 63/210,800, filed on Jun. 15, 2021.

(51) Int. Cl.
 *C12Q 1/48* (2006.01)

(52) U.S. Cl.
 CPC ..... *C12Q 1/48* (2013.01); *G01N 2333/91051* (2013.01); *G01N 2500/02* (2013.01)

(58) Field of Classification Search
 None
 See application file for complete search history.

(56) References Cited

U.S. PATENT DOCUMENTS

| | | | |
|---|---|---|---|
| 5,525,479 | A | 6/1996 | Anthony et al. |
| 2009/0208990 | A1 | 8/2009 | Deschenes et al. |
| 2014/0024061 | A1 | 1/2014 | Auerbach et al. |
| 2015/0018520 | A1 | 1/2015 | Hougland |
| 2015/0057236 | A1* | 2/2015 | Lin ............ C07D 405/06 435/23 |
| 2017/0056373 | A1 | 3/2017 | Hougland |
| 2018/0200250 | A1 | 7/2018 | Deschenes et al. |
| 2021/0032298 | A1 | 2/2021 | Sharma et al. |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession AAP60117. Jan. 1, 1980 (Year: 1980).*
Darling, J.E., et al., "A fluorescent peptide substrate facilitates investigation of ghrelin recognition and acylation by ghrelin O-acyltransferase", Analytical Biochemistry (2013), Received Dec. 26, 2012, Received in revised form Feb. 12, 2013, Accepted Feb. 16, 2013, Available online Feb. 27, 2013, pp. 68-76, 437.
Ducker, C.E., et al., "In vitro and cellular assays for palmitoyl acyltransferases using fluorescent lipidated peptides", Methods, Oct. 2006, pp. 166-170, 40(2).
Hamel, L.D., et al., "A fluorescence-based assay to monitor autopalmitoylation of zDHHC proteins applicable to high-throughput screening", Analytical Biochemistry, Article history Received Apr. 19, 2014, Received in revised form May 13, 2014, Accepted May 16, 2014, Available online May 27, 2014, pp. 1-8, 460.
Hong, J.Y., et al., "High-Throughput Enzyme Assay for Screening Inhibitors of the ZDHHC3/7/20 Acyltransferases", ACS Chemical Biology, 2021, Received Apr. 6, 2021, Accepted Aug. 4, 2021, Published Aug. 10, 2021, pp. 1318-1324, 16.
Lanyon-Hogg, T., et al., "Acylation-coupled lipophilic induction of polarisation (Acyl-CLIP): a universal assay for lipid transferase and hydrolase enzymes", Chem. Sci., 2019, Received Apr. 11, 2019 Accepted Jun. 16, 2019, pp. 8995-9000, 10.
Mitchell, D.A., et al., "In Vitro Assays to Monitor the Enzymatic Activities of zDHHC Protein Acyltransferases", Maurine E. Linder (ed.), Protein Lipidation: Methods and Protocols, Methods in Molecular Biology, 2019, pp. 169-177, Chapter 13, vol. 2009.
Salaun, C., et al., "Development of a novel high-throughput screen for the identification of new inhibitors of protein S-acylation", Received for publication Mar. 18, 2022, in revised form, Aug. 24, 2022 Published, Papers in Press, Sep. 8, 2022, J. Biol. Chem. (2022), pp. 1-22, 298, (10) 102469.
Simanshu, D.K., et al., "RAS Proteins and Their Regulators in Human Disease", Cell, Jun. 29, 2017, pp. 17-33, 170.

* cited by examiner

*Primary Examiner* — Christian L Fronda
(74) *Attorney, Agent, or Firm* — Scully, Scott, Murphy & Presser, P.C.

(57) ABSTRACT

A method for determining activity of an acyl transferase enzyme, the method comprising: (i) preparing a reaction mixture comprising: (a) an acyl transferase enzyme, (b) a peptide substrate bound to a fluorophore, wherein the substrate is a cysteine-containing oligopeptide of 5-25 amino acids in length, (c) an acyl-CoA, and (d) a detergent comprising micelles, wherein the acyl transferase enzyme mediates acylation on a cysteine of said peptide substrate to result in association of the peptide with micelles of the detergent with resultant increase in fluorescence polarization; and (ii) measuring fluorescent signal of the reaction mixture; wherein an increase in fluorescence polarization of the reaction mixture compared to fluorescence polarization of a control reaction indicates acyl transferase activity of the acyl transferase enzyme. The above assay method may also be used for screening compounds for their ability to act as inhibitors of an acyl transferase enzyme.

9 Claims, 4 Drawing Sheets

Specification includes a Sequence Listing.

HIGH-THROUGHPUT ENZYME ASSAY FOR SCREENING ACTIVITY OF ACYLTRANSFERASES

CROSS-REFERENCE TO RELATED APPLICATIONS

This application claims priority from U.S. Provisional Application No. 63/210,800, filed Jun. 15, 2021, which is herein incorporated by reference in its entirety.

INCORPORATION BY REFERENCE OF SEQUENCE LISTING

The Sequence Listing in .txt format, named as 39726_9935-02-US_SequenceListing of 1 KB, created on Dec. 12, 2023, and submitted to the United States Patent and Trademark Office via Patent Center, is incorporated herein by reference.

STATEMENT REGARDING FEDERALLY SPONSORED RESEARCH

This invention was made with government support under Contract No. R01GM121540 awarded by the National Institutes of Health. The government has certain rights in the invention.

BACKGROUND OF THE DISCLOSURE

Protein acylation is a post-translational modification in which an acyl transferase (lipid transferase) enzyme attaches a fatty acyl group to a protein substrate. The acylation may be, for example, S- or N-palmitoylation, N-myristoylation, S-farnesylation or S-geranylgeranylation. Protein cysteine palmitoylation (S-palmitoylation), in particular, is a post-translational modification in which a long chain 16:0 carbon palmitoyl group attaches to a cysteine. This modification regulates membrane localization and trafficking of proteins, as well as protein stability and protein-protein interactions. Several thousand proteins are known to be modified by S-palmitoylation, making it a very abundant modification affecting numerous biological pathways.

S-palmitoylation is reversible and often there exists a dynamic cycle of addition and removal of the palmitoyl group. Known protein cysteine palmitoyltransferases belong to the ZDHHC (zinc finger Asp-His-His-Cys) family of enzymes that primarily use palmitoyl-CoA as the acyl donor. In the reaction mechanism, the cysteine of the DHHC motif in the cytosolic region initially gets auto-palmitoylated and then the palmitoyl group is transferred to the cysteine of the target proteins (L. H. Chamberlain et al., *Physiol. Rev.*, 95, 341-376, 2015). S-palmitoylation can be reversed by several proteins, including acyl protein thioesterase 1 and 2 (APT1 and APT2), alpha/beta hydrolase domain (ABHD)-containing proteins ABHD17A/B/C, and ABHD10 (J. A. Duncan et al., *J. Biol. Chem.*, 277, 31740-31752, 2002).

Since attachment of long-chain acyl groups to substrate proteins has been implicated in a number of diseases and disorders, such as cancer and neurodegeneration, there has been a continued effort in identifying inhibitors of acylation. ZDHHC proteins, in particular, have been reported to be promising therapeutic targets for treating cancer and autoimmune diseases. Yet, due to the lack of potent selective inhibitors, scrutiny of the biological functions of ZDHHCs has been limited. An inhibitor presently available is 2-bromopalmitate (2-BP), which forms a covalent bond with the cysteine in the DHHC motif (B. C. Jennings et al., *J. Lipid Res.*, 50, 233-242, 2009). However, 2-BP has several disadvantages, including its ability to inhibit the known ZDHHCs and various other proteins in an unselective manner.

The main hindrance for developing ZDHHC inhibitors is the lack of a facile high-throughput assay. The most frequently used in vitro assay utilizes radioactive palmitoyl-CoA to examine the transfer of the radioactive palmitate to specific substrate proteins. However, this assay is cumbersome, time-consuming, and difficult to use in a high-throughput manner. A click chemistry-based high-throughput screening assay was developed, but it requires a farnesylated Ras peptide that is cumbersome to synthesize, and the click chemistry approach adds multiple sample processing steps after the enzymatic reaction.

BRIEF SUMMARY OF THE DISCLOSURE

The present disclosure provides a high-throughput assay for determining the activity of acyl transferases, particularly ZDHHC acyl transferases. Using the assay method, a large number of potential acyl transferase inhibitors can be rapidly screened. As discussed later in this disclosure, it has herein been demonstrated that in vitro results from the assay are supported by results from cell-based assays. The novel assay methods described herein will accelerate the high-throughput screening of large compound libraries in the search for improved acyl transferase inhibitors, which will help identify new leads in the treatment of cancer and autoimmune diseases In a first aspect, the present disclosure provides an assay method for determining the activity of an acyl transferase enzyme, particularly a ZDHHC acyl transferase. The method includes the following steps: (i) preparing a reaction mixture comprising: (a) an acyl transferase enzyme (e.g., a ZDHHC enzyme), (b) a peptide substrate bound to a fluorophore, wherein the substrate is a cysteine-containing oligopeptide of 5-25 amino acids in length, (c) an acyl-CoA (e.g., palmitoyl-CoA), and (d) a detergent (surfactant) comprising micelles, wherein the acyl transferase enzyme mediates acylation on a cysteine of the peptide substrate to result in association of the acylated peptide with micelles of the detergent with resultant increase in fluorescence polarization; and (ii) measuring fluorescent signal of the reaction mixture; wherein an increase in fluorescence polarization of the reaction mixture compared to fluorescence polarization of a control reaction indicates acyl transferase activity of the acyl transferase enzyme.

In a second aspect, the present disclosure provides an assay method for screening candidate compounds as inhibitors of acyl transferase activity, particularly a ZDHHC acyl transferase. The method includes the following steps: (i) preparing a reaction mixture comprising: (a) an acyl transferase enzyme, (b) a peptide substrate bound to a fluorophore, wherein the substrate is a cysteine-containing oligopeptide of 5-25 amino acids in length, (c) an acyl-CoA, (d) a detergent comprising micelles, and (e) a candidate compound; wherein the acyl transferase enzyme mediates acylation on said peptide substrate to result in association of the peptide substrate with micelles of the detergent with resultant increase in fluorescence polarization; and (ii) measuring the fluorescent signal of the reaction mixture; wherein a decrease in fluorescence polarization of the reaction mixture compared to fluorescence polarization of a control reaction not containing said candidate compound indicates that the candidate compound inhibits acyl transferase.

In a third aspect, the present disclosure provides a kit for practicing any of the assay methods described above. In particular embodiments, the kit includes the following components: (i) an acyl transferase enzyme; (ii) a peptide substrate bound to a fluorophore, wherein the substrate is a cysteine-containing oligopeptide of 5-25 amino acids in length; (iii) an acyl-CoA; and (iv) a detergent. The kit may or may not further include a buffer, a pH adjuster, and/or a disulfide reducing agent. The components of the kit may be used to determine the activity of an acyl transferase enzyme, or more particularly, determine the ability of a candidate compound to inhibit an acyl transferase enzyme by any of the assay methods described above.

In a fourth aspect, the present disclosure provides inhibitor compounds containing a fatty acyl portion, with halogen substitution at the alpha position. The halogen is typically selected from chlorine, bromine, and iodine. The fatty acyl compound may be, for example, a fatty acyl ketone, fatty acyl ester, fatty acyl thioester, or fatty acyl amide, all of which contain an alpha-halogen, such as depicted in any of Formulas (1), (1a), (1b), (1c), and (1d) below.

BRIEF DESCRIPTION OF THE FIGURES

FIG. 2A shows the results for ZDHHC7; FIG. 2B shows the results for ZDHHC3; and FIG. 2C shows the results for ZDHHC20. In 0.1% DDM and MES buffer, 0.3 µM ZDHHC7 or 0.6 µM ZDHHC3/20 was incubated with palmitoyl-CoA, TCEP, and FAM-KRas4a peptide substrate for 1 hour (ZDHHC7) or 2.5 hours (ZDHHC3/20). The real-time monitoring of the fluorescence anisotropy was measured by Cytation 5.

FIG. 4A demonstrates Alk14 labeling and in-gel fluorescence to detect STAT3 acylation induced by ZDHH7 in HEK 293T cells. Cells were treated with 50 µM of the inhibitors for the indicated hours and labeled with 50 µM of Alk-14 for 6 hours. FIG. 4B demonstrates Alk14 labeling and in-gel fluorescence to detect STAT3 acylation induced by ZDHHC3 in HEK293T cells. Cells were treated with 25 µM of inhibitors for 16 hours and labeled with 50 µM of Alk-14 for 6 hours. Relative FL/Protein for both experiments was calculated by dividing fluorescence signal by the protein level from the corresponding "CBB" lane. The fatty acylation level of DMSO with Alk14 was set to 1.

DETAILED DESCRIPTION OF THE DISCLOSURE

Figure 1:
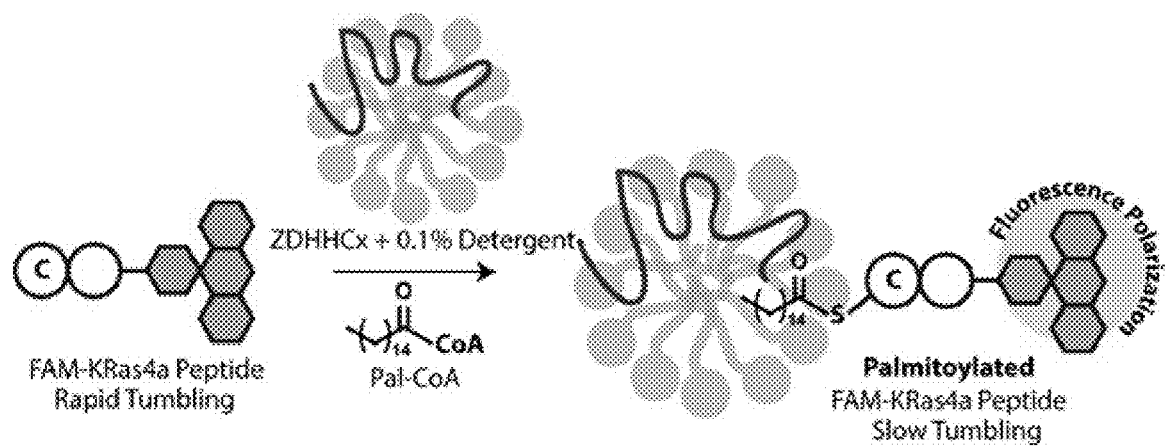
FIG. 1. Graphical scheme of the Acyl-cLIP ZDHHC assay. The acylation of the peptide by the ZDHHC enzyme facilitates binding of the peptide to detergent micelles, which slows down the tumbling and increases the fluorescence polarization.

In this disclosure, the term "amino acid" is intended to embrace all molecules, whether natural or synthetic, that include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. In some embodiments, the term "amino acid" refers only to the twenty known essential amino acids, or a subset thereof, i.e., glycine (G), alanine (A), valine (V), leucine (L), isoleucine (I), cysteine (C), methionine (M), phenylalanine (F), tyrosine (Y), tryptophan (W), proline (P), serine (S), threonine (T), asparagine (N), glutamine (Q), aspartic acid (D), glutamic acid (E), histidine (H), lysine (K), and arginine (R). In some embodiments, one or more of any of the foregoing classes or specific types of amino acids are excluded.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing. They may include one or more types of any of the amino acid residues described above, or a modified form thereof, and typically include at least 10, 20, 30, 40, or 50, and up to 80, 100, 120, 150, 200, 300, 400, 500, or 1,000 amino acid residues. The term "oligopeptide", as used herein, generally refers to a chain of amino acid residues of at least 4, 5, or 6 and typically up to 8, 10, 15, 20, 25, or 30.

As used herein, the term "hydrocarbon group" (also denoted by the group R) is, in a first embodiment, composed solely of carbon and hydrogen. The hydrocarbon group may contain, for example, one, two, three, four, five, six, seven, eight, nine, ten, eleven, or twelve carbon atoms, or a number of carbon atoms within a range therein (e.g., 1-12, 2-12, or 3-12 carbon atoms). The hydrocarbon group composed solely of carbon and hydrogen can be, for example, an alkyl, alkenyl, cycloalkyl, cycloalkenyl (aliphatic), or aromatic group.

Some examples of straight-chained (linear) alkyl groups include methyl, ethyl, n-propyl, n-butyl, n-pentyl, n-hexyl, n-heptyl, n-octyl, n-nonyl, n-decyl, n-undecyl, and n-dodecyl groups. Some examples of branched alkyl groups include isopropyl (2-propyl), isobutyl (2-methylprop-1-yl), sec-butyl (2-butyl), t-butyl, 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, and isohexyl (4-methylpent-1-yl), wherein the "1-yl" suffix represents the point of attachment of the group.

Some examples of straight-chained olefinic (alkenyl) groups include vinyl, propen-1-yl (allyl), 3-buten-1-yl ($CH_2$=CH—$CH_2$—$CH_2$—), 2-buten-1-yl ($CH_2$—CH=CH—$CH_2$—), butadienyl, and 4-penten-1-yl groups. Some examples of branched olefinic groups include propen-2-yl, 3-buten-2-yl ($CH_2$=CH—CH.—$CH_3$), 3-buten-3-yl ($CH_2$=C.—$CH_2$—$CH_3$), 4-penten-2-yl, 4-penten-3-yl, 3-penten-2-yl, 3-penten-3-yl, and 2,4-pentadien-3-yl, wherein the dot in the foregoing exemplary formulas represents a radical (i.e., the point of attachment of the group).

Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkenyl (aliphatic) groups include cyclopropenyl, cyclobutenyl, cyclopentenyl, cyclopentadienyl, cyclohexenyl, cyclohexadienyl, cycloheptenyl, cycloheptadienyl, cyclooctenyl, cyclooctadienyl, and cyclooctatetraenyl groups. Some examples of aromatic groups include phenyl and benzyl. The aromatic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene.

In another embodiment, the term "hydrocarbon group" (R) contains at least one heteroatom (i.e., non-carbon and non-hydrogen atom), such as one or more heteroatoms selected from oxygen, nitrogen, sulfur, and halide atoms, or groups containing one or more of these heteroatoms (i.e., heteroatom-containing groups). One or more of the heteroatoms (e.g., oxygen, nitrogen, and/or sulfur atoms) can be inserted between carbon atoms (e.g., as —O—, —NR'—, or —S—) in any of the hydrocarbon groups described above. Alternatively, or in addition, one or more of the heteroatom-containing groups can replace one or more hydrogen atoms on the hydrocarbon group. In some embodiments, the hydrocarbon group contains at least one halogen atom (such as in —CF$_3$).

Some examples of oxygen-containing groups include hydroxy (OH), alkoxy (OR), carbonyl-containing (e.g., carboxylic acid, ketone, aldehyde, carboxylic ester, amide, and urea functionalities), nitro (NO$_2$), carbon-oxygen-carbon (ether), sulfonyl, and sulfinyl (i.e., sulfoxide) groups. Some particular examples of alkoxy groups (—OR) include methoxy, ethoxy, n-propoxy, isopropoxy, n-butoxy, isobutoxy, t-butoxy, phenoxy, benzyloxy, 2-hydroxyethoxy, 2-methoxyethoxy, 2-ethoxyethoxy, vinyloxy, and allyloxy groups. In the case of an ether group, the ether group can also be a polyalkyleneoxide (polyalkyleneglycol) group, such as a polyethyleneoxide group. Some examples of nitrogen-containing groups include primary amine, secondary amine, tertiary amine (i.e., —NR'2, wherein R' is independently selected from H and hydrocarbon groups set forth above), nitrile (CN), amide (i.e., —C(O)NR'2 or —NRC(O)R', wherein R' is independently selected from hydrogen atom and hydrocarbon groups set forth above), imine (e.g., —CR'=NR', wherein R' is independently H or a hydrocarbon group), urea (—NR'—C(O)—NR'2, wherein R' is independently H or a hydrocarbon group), and carbamate groups (—NR'—C(O)—OR', wherein R' is independently H or a hydrocarbon group). Some examples of sulfur-containing groups include mercapto (i.e., —SH), thioether (i.e., sulfide, e.g., —SR), disulfide (—R—S—S—R), sulfoxide (—S(O)R), sulfone (—SO$_2$R), sulfonate (—S(=O)$_2$OR'', wherein R'' is H, a hydrocarbon group, or a cationic group), and sulfate groups (—OS(=O)$_{20}$R'', wherein R'' is H, a hydrocarbon group, or a cationic group). Some examples of halide atoms include fluorine, chlorine, bromine, and iodine.

In some embodiments, any of the generic substituents (e.g., R, R$_1$, R$_2$, and the like) described anywhere in this disclosure may independently exclude any one or more of the classes, subclasses, or particular hydrocarbon groups described above, or may independently include only specific hydrocarbon groups selected from the hydrocarbon groups (R) described above.

The term "acyl transferase enzyme" includes any of the classes of acyl transferase enzymes, unless otherwise specified. Some examples of classes of acyl transferase enzymes include palmitoyl transferases (e.g., ZDHHC acyl transferases), glyceronephosphate O-acyltransferase, lecithin-cholesterol acyl transferase, and long-chain-alcohol 0-fatty-acyl transferase. In particular embodiments, the acyl transfer enzyme is a ZDHHC acyl transferase enzyme, which mediates S-acylation on a cysteine of a protein substrate. The ZDHHC family of S-acyltransferases is described in detail in K. Lemonidis et al., *Biochem. Soc. Trans.*, 43(2), 217-221, April 2015, the contents of which are herein incorporated by reference.

The term "peptide substrate," as used herein, refers to a cysteine-containing oligopeptide that can function as a substrate for an acyl transferase enzyme, such as any of the acyl transferases described above, particularly a palmitoyl transferase or ZDHHC acyl transferase. The peptide substrate contains precisely one cysteine or at least one cysteine. For purposes of the present invention, the peptide substrate is typically 5-25 amino acids in length. In various embodiments, the peptide substrate is 5, 6, 7, 8, 9, 10, 11, 12, 13, 14, 15, 16, 17, 18, 19, 20, 21, 22, 23, 24, or 25 amino acids in length, or the peptide substrate has a number of amino acids within a range bounded by any two of the foregoing amino acid numbers, e.g., 5-22, 5-21, 5-20, 5-19, 5-18, 5-17, 5-16, 5-15, 11-22, 11-21, 11-20, 11-19, 11-18, 11-17, 11-16, or 11-15. In some embodiments, the peptide substrate is a peptide fragment of a Ras family protein. As well documented in the art (e.g., D. K. Simanshu et al., Cell, 170, Jun. 29, 2017; E. Santos et al., FASEB J., 3 (10), 2151-2163, 1989; and C. W. Han et al., *BMB Rep.* 50 (7): 355-360, 2017), the Ras (from Rat sarcoma virus) family proteins are small GTPases involved in cellular signal transduction. Ras family proteins contain a G domain of about 20 kDa that binds guanosine nucleotides and a C-terminal membrane targeting region (CAAX—COOH, also known as CAAX motif), which is lipid-modified by farnesyl transferase. In some embodiments, the peptide substrate excludes or is modified to exclude a CAAX motif, wherein C is an invariant cysteine (C), A is an aliphatic amino acid, and X is a variable amino acid in the terminal position. The CAAX motif is typically present at the carboxy-terminus of some peptide substrates, particularly those having a Ras peptide sequence. In some embodiments, the peptide substrate includes the amino acid sequence ISKEEKTPGCVKIKK (SEQ ID NO: 1), wherein up to five amino acids in the sequence other than cysteine (C) may be replaced with other amino acids. In some embodiments, one, two, three, four, or five amino acids in the sequence other than cysteine (C) may be replaced with other amino acids. In some embodiments, not more than 3 amino acids in the sequence other than cysteine (C) are replaced with other amino acids. In some embodiments, not more than 2 amino acids in the sequence other than cysteine (C) are replaced with other amino acids. In some embodiments, only 1 amino acid in the sequence other than cysteine (C) is replaced with another amino acid. In embodiments where one or more amino acids in the sequence are replaced with other amino acids, the replacement is a conservative substitution. In some embodiments, the peptide substrate has an invariant 15-mer ISKEE-KTPGCVKIKK (SEQ ID NO: 1) sequence.

For purposes of the invention, the peptide substrate is bound to a fluorophore. The fluorophore can be any of the organic molecules or inorganic particles known in the art having an ability to fluoresce when stimulated with electromagnetic radiation of suitable wavelength. The term "fluorescent species" may also herein be used interchangeably with the term "fluorophore". The fluorophores considered herein can absorb and emit light of any suitable wavelength. In some embodiments, it may be desired to select a fluorophore with particular absorption and emission characteristics. For example, in different embodiments, the fluorophore absorbs at nanometer (nm) wavelengths of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 nm, or within a range bounded by any two of the foregoing values.

In different embodiments, the fluorophore emits at any of the foregoing wavelengths, or within a range bounded by any two of the foregoing values, wherein it is understood that a fluorophore generally emits at a longer wavelength than the absorbed wavelength. The impinging electromagnetic radiation (i.e., which is absorbed by the fluorophore) can be in a dispersed form, or alternatively, in a focused form, such as a laser. Moreover, the absorbed or emitted radiation can be in the form of, for example, far infrared, infrared, far red, visible, near-ultraviolet, or ultraviolet.

In a first set of embodiments, the fluorophore is an organic molecule, which generally contains at least one carbon-carbon bond and at least one carbon-hydrogen bond. In different embodiments, the organic fluorophore can include, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). In the particular case of unsaturated fluorophores, the fluorophore contains one, two, three, or more carbon-carbon and/or carbon-nitrogen double and/or triple bonds. In a particular embodiment, the fluorophore contains at least two (e.g., two, three, four, five, or more) conjugated double bonds (i.e., a polyene linker) aside from any aromatic group that may be in the fluorophore. In other embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups. In some embodiments, the fluorophore contains a polyalkyleneoxide group that contains at least two, three, or four alkyleneoxide units. In other embodiments, the fluorophore contains at least one sulfonic acid or sulfonate salt group.

In some embodiments, the organic fluorophore is a xanthene derivative (e.g., fluorescein, carboxyfluorescein, rhodamine, Oregon green, eosin, and Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), naphthalene derivatives (e.g., dansyl and prodan derivatives), coumarin and its derivatives, oxadiazole and its derivatives (e.g., pyridyloxazoles, nitrobenzoxadiazoles, and benzoxadiazoles), pyrene and its derivatives, oxazine and its derivatives (e.g., Nile Red, Nile Blue, and cresyl violet), acridine derivatives (e.g., proflavin, acridine orange, and acridine yellow), arylmethine derivatives (e.g., auramine, crystal violet, and malachite green), and tetrapyrrole derivatives (e.g., porphyrins and bilirubins).

In some embodiments, the fluorophore is a streptocyanine (open chain cyanine) having the general structure:

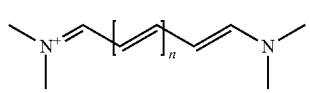

(1)

wherein n can be, for example, 0, 1, 2, 3, 4, 5, 6, 7, or 8, or a value within a range therein. Other structures related to or derived from Formula (1) are also considered herein, as amply described in Guieu, V., et al., Eur. J. Org. Chem., 2007, 804-810, which is incorporated herein by reference in its entirety.

In other embodiments, the fluorophore is a hemicyanine having the general structure:

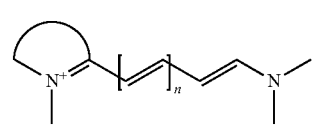

(2)

wherein n in formula (2) is as defined above. The arc in Formula (2) indicates a nitrogen-containing ring, such as pyrrolyl. The arc may alternatively represent a bicyclic ring system, such as a benzopyrrolyl fused ring system. Other structures related to or derived from formula (2) are also considered herein, as amply described in Stathatos, E., et al. Chem. Mater., 2001, 13, 3888-3892, and Yao, Q.-H., et al. J. Mater. Chem., 2003, 13, 1048-1053, which are incorporated herein by reference in their entirety.

In other embodiments, the fluorophore is a closed cyanine having the general structure:

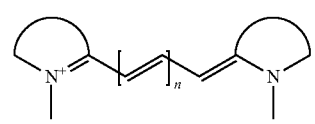

(3)

wherein n in formula (3) is as defined above.

In other embodiments, the fluorophore is a cyanine dye (i.e., cyanine-based fluorophore). The term "cyanine dye", as used herein, refers to any of the dyes, known in the art, that include two indolyl or benzoxazole ring systems interconnected by a conjugated polyene linker. The cyanine dye typically contains at least two or three conjugated carbon-carbon double bonds, at least one of which is not in a ring, such as depicted in any of Formulas (1)-(3). The cyanine dye (or other type of dye) often contains at least two pyrrolyl rings. Some particular examples of cyanine dyes are the Cy® family of dyes, which include, for example, Cy2, Cy3, Cy3B, Cy3.5, Cy5, Cy5.5, Cy7, and Cy9. The term "cyanine moiety", as used herein, generally includes the bis-indolyl-polyene or bis-benzoxazolyl-polyene system, but excludes groups attached to the ring nitrogen atoms in the indolyl or benzoxazolyl groups. The cyanine dyes may also include the Alexa® family of dyes (e.g., Alexa Fluor 350, 405, 430, 488, 500, 514, 532, 546, 555, 568, 594, 610, 633, 647, 660, 680, 700, 750, and 790), the ATTO® family of dyes (e.g., ATTO 390, 425, 465, 488, 495, 520, 532, 550, 565, 590, 594, 601, 615, 619, 629, 635, 645, 663, 680, 700, 729, and 740), and the Dy® family of dyes (e.g., DY 530, 547, 548, 549, 550, 554, 556, 560, 590, 610, 615, 630, 631, 631, 632, 633, 634, 635, 636, 647, 648, 649, 650, 651, 652, 675, 676, 677, 680, 681, 682, 700, 701, 730, 731, 732, 734, 750, 751, 752, 776, 780, 781, 782, and 831). The ATTO dyes, in particular, can have several structural motifs, including, coumarin-based, rhodamine-based, carbopyronin-based, and oxazine-based structural motifs.

The fluorophore may alternatively be an inorganic fluorophore, such as a metal, metal oxide, or quantum dot nanoparticle or microparticle capable of fluorescing when stimulated. The fluorescing ability may be an innate property arising from the composition of the particle, or the fluorescing ability may arise from fluorophore doping or surface conjugation to an organic fluorophore species. The fluorescent dopant may be, for example, a lanthanide ion, such as, Ce, Er, Gd, Dy, or Yb. Some examples of metal particle fluorophores include gold and silver particles. Some examples of metal oxide fluorescent particles include fluorophore-doped silica, titania, or zirconia particles. Some examples of quantum dot nanoparticles include particles having a zinc sulfide, zinc selenide, zinc telluride, cadmium sulfide, cadmium selenide, or cadmium telluride composition. A detailed description of fluorescent nanoparticles is provided in 0. S. Wolfbeis, *Chem. Soc. Rev.*, 44, 4743-4768, 2015, the contents of which are herein incorporated by reference in their entirety.

The term "acyl-CoA", as used herein, refers to any of the co-enzymes, well known in the art, involved in the metabolism and oxidation of fatty acids, wherein CoA refers to Coenzyme A. The acyl group in the acyl-CoA is typically connected to CoA via a thioester bond. The acyl-CoA may be depicted by the structure R'C(O)S-CoA, wherein R' is typically a saturated alkyl group containing 12-24 carbon atoms. The acyl-CoA may be, more particularly, for example, a palmitoyl-CoA, stearoyl-CoA, oleyl-CoA, arachidonyl-CoA, behenyl-CoA, or myristoyl-CoA.

The term "detergent," as used herein, includes any surfactant (surface active) compound capable of producing micelles in aqueous solution. The surfactant may be ionic or non-ionic. As well known, such compounds produce micelles at a critical micelle concentration (CMC). The surface active agent may be, for example, a natural or synthetic polymer. The surface active agent it typically amphiphilic by containing one or more hydrophilic portions and one or more hydrophobic sections. Some examples of amphiphilic surface active agents include sodium lauryl sulfate, alkylbenzene sulfonates, and lignin sulfonates. In some embodiments, the surface active agent is a natural-based surfactant, and may be based on a polypeptide (e.g., protein), monosaccharide, disaccharide, or polysaccharide (sugar or carbohydrate). Some examples of monosaccharide surfactants include n-decyl glucoside and glucose laurate. Some examples of disaccharide surfactants include n-decyl β-D-maltoside n-dodecyl β-D-maltoside (DDM), sucrose laurate, and sucrose monostearate. Some examples of polysaccharide surface active agents include dextran, dextrose, starch, maltodextrin, chitosan, pectin, agarose, hemicellulose (e.g., xylan), alginate, carrageenan, guar gum, xanthan gum, locust bean gum, and cellulose gum. Some examples of synthetic polymers include polyvinyl alcohol, polyvinyl acetate, and polysorbate-type non-ionic surfactants (e.g., polysorbate 80).

In some embodiments, the detergent (surfactant) contains at least one polyalkylene oxide (hydrophilic) portion attached to a hydrophobic hydrocarbon portion. The polyalkylene oxide (PAO) portion is typically polyethylene oxide (PEO), although polypropylene oxide (PPO), and polybutylene oxide (PBO) may also serve as the PAO. The PAO typically includes at least or greater than 5, 10, 15, 20, 30, 40, or 50 alkylene oxide units. As part of the hydrophilic portion, the surfactant may alternatively or in addition include one or more hydroxy (OH) or cyclic ether (e.g., tetrahydrofuran) groups per molecule. The hydrocarbon portion is generally constructed solely of carbon and hydrogen atoms, except that one or more fluorine atoms may or may not be present. The hydrocarbon portion may be or include one or more alkyl groups, alkenyl groups, cycloalkyl groups, and aromatic groups (e.g., phenyl). In some embodiments, the surfactant includes a hydrocarbon group corresponding to a linear or branched hexyl, heptyl, octyl, nonyl, decyl, undecyl, or dodecyl group. Some examples of these types of surfactants include: (i) Triton® X-100 and Igepal® surfactants, which contain a (1,1,3,3-tetramethylbutyl)phenyl portion; (ii) polysorbate (Tween®) surfactants, such as polysorbate 80, which contain a polyethoxylated sorbitan moiety attached (typically via an ester bond) to a hydrocarbon group, such as an undecyl group; (iii) non-ionic triblock copolymers, also known as poloxamers, such as Pluronic® surfactants, which typically contain alternating PEO and PPO units, such as PEO-PPO-PEO and PPO-PEO-PPO surfactants; and (iv) Brij® surfactants, which contain a PEO portion attached to an alkyl portion (typically 12-20 carbon atoms).

In a first assay method, the level of activity of an acyl transferase enzyme is determined. The method involves first preparing a reaction mixture that includes at least the following components: (a) an acyl transferase enzyme, which may be any of the acyl transferase enzymes described above, such as a ZDHHC acyl transferase enzyme; (b) a peptide substrate bound to a fluorophore, wherein the substrate is a cysteine-containing oligopeptide of 5-25 amino acids in length, such as any of those described above; (c) an acyl-CoA, such as any of the acyl-CoAs described above, such as a palmitoyl-CoA; and (d) a detergent, such as any of those described above, that forms micelles in the reaction mixture. In some embodiments, the reaction mixture consists of only components (a)-(d). In other embodiments, the reaction mixture may include one or more auxiliary components, such as a buffer, pH modifier or adjuster, or disulfide bond reducing agent (e.g., TCEP), provided the additional component(s) are compatible with the other components and do not hinder the objective of the method to determine the level of activity of an acyl transferase enzyme. The buffer may be, for example, 2-(N-morpholino)ethanesulfonic (MES), 3-(N-morpholino)propanesulfonic (MOPS), Tris, or HEPES. Notably, to ensure the presence of micelles, the detergent should be present in the reaction mixture in a concentration at least or above the critical micelle concentration (CMC) of the detergent. The concentration of the detergent may be, for example, at least or above 0.01, 0.02, 0.03, 0.04, 0.05, 0.06, 0.07, 0.08, 0.09, 0.1, 0.12, 0.15, 0.18, 0.2, 0.22, 0.25, 0.3, 0.35, or 0.4 v/v % or w/w %, or the concentration is within a range bounded by any two of the foregoing values (e.g., 0.01-2 v/v % or v/w %), depending on the CMC of the detergent. Any of the foregoing concentrations may alternatively be taken as mM values. In some embodiments, the acyl transferase enzyme primarily uses palmitoyl-CoA as an acyl donor. In particular embodiments, the acyl transferase enzyme is a palmitoyl transferase, and the acyl-CoA is palmitoyl-CoA.

Once the reaction mixture is prepared, the acyl transferase enzyme mediates acylation on a cysteine of the peptide substrate to result in an acylated peptide. As a result of the acylation on the peptide substrate, the peptide (i.e., now acylated) associates with micelles of the detergent via the acyl fatty portion on the peptide substrate, as schematically shown in FIG. 1. As a result of the association of the peptide substrate with the micelles, the fluorophore on the peptide substrate has a decreased freedom of movement which slows down the tumbling and increases the fluorescence polarization. The increase in fluorescence polarization can be detected by conventional fluorescence anisotropy detection and used as a means for confirming acylation activity and also determining the level of acylation activity since a greater increase in fluorescence polarization corresponds to a greater level of acylation activity. The fluorescence signal (i.e., polarization) of the reaction mixture is measured and compared to the fluorescence polarization of a control reaction to determine the level of acyl transferase activity of the acyl transferase enzyme. The control reaction of the first assay method contains the peptide substrate attached to the fluorophore under conditions where acylation does not occur. In one embodiment, the control reaction contains the same components of the reaction mixture, except that the control reaction does not contain the acyl transferase enzyme. In another embodiment, the control reaction contains the same components of the reaction mixture, including the acyl transferase enzyme, but the acyl transferase enzyme is inhibited or incapacitated (e.g., by including a known inhibitor of the enzyme, or by being denatured or reaction center removed or modified).

In a second assay method, the level of activity of an acyl transferase enzyme is determined as above, except in the presence of a potential inhibitor compound (candidate compound). If the fluorescence polarization decreases in the presence of the candidate compound, the candidate compound is identified as an inhibitor compound of the acyl transferase enzyme. Notably, the method is further useful for determining the degree of inhibition possessed by the candidate compound. The method involves first preparing a reaction mixture that includes at least the following components: (a) an acyl transferase enzyme, which may be any of the acyl transferase enzymes described above, such as a ZDHHC acyl transferase enzyme; (b) a peptide substrate bound to a fluorophore, wherein the substrate is a cysteine-containing oligopeptide of 5-25 amino acids in length, such as any of those described above; (c) an acyl-CoA, such as any of the acyl-CoAs described above, such as a palmitoyl-CoA; (d) a detergent, such as any of those described above, that forms micelles in the reaction mixture; and (e) a candidate compound. In some embodiments, the reaction mixture consists of only components (a)-(e). In other embodiments, the reaction mixture may include one or more auxiliary components, such as a buffer, pH modifier or adjuster, or disulfide bond reducing agent (e.g., TCEP), provided the additional component(s) are compatible with the other components and do not hinder the objective of the method to determine the inhibitory ability of a candidate compound. The buffer may be, for example, 2-(N-morpholino)ethanesulfonic (MES), 3-(N-morpholino)propanesulfonic (MOPS), Tris, or HEPES. To ensure the presence of micelles, the detergent should be present in the reaction mixture in a concentration at least or above the critical micelle concentration (CMC) of the detergent. The concentration of the detergent may be, for example, at least or above 0.01, 0.02, 0.03, 0.04, 0.05, 0.06, 0.07, 0.08, 0.09, 0.1, 0.12, 0.15, 0.18, 0.2, 0.22, 0.25, 0.3, 0.35, or 0.4 v/v % or w/v %, or the concentration is within a range bounded by any two of the foregoing values (e.g., 0.01-2 v/v % or v/w %), depending on the CMC of the detergent. Any of the foregoing concentrations may alternatively be taken as mM values. In some embodiments, the acyl transferase enzyme primarily uses palmitoyl-CoA as an acyl donor. In particular embodiments, the acyl transferase enzyme is a palmitoyl transferase, and the acyl-CoA is palmitoyl-CoA.

Once the reaction mixture is prepared, the acyl transferase enzyme mediates acylation on a cysteine of the peptide substrate. As a result of the acylation on the peptide substrate, the peptide substrate associates with micelles of the detergent via the acyl fatty portion on the peptide substrate, as schematically shown in FIG. 1. As a result of the association of the peptide substrate with the micelles, the fluorophore on the peptide substrate has a decreased freedom of movement which slows down the tumbling and increases the fluorescence polarization. The detection of the fluorescence polarization has been described above. The fluorescence signal (i.e., polarization) of the reaction mixture is measured and compared to the fluorescence polarization of a control reaction to determine the level of activity of the acyl transferase enzyme. The control reaction of the second assay method contains the same components of the reaction mixture, except that the control reaction does not contain the candidate compound. A decrease in fluorescence polarization of the reaction mixture compared to fluorescence polarization of the control reaction not containing the candidate compound indicates that the candidate compound inhibits the acyl transferase, and the degree of inhibition provided by the candidate compound can be quantified by measuring the degree of fluorescence polarization relative to the control reaction.

In another aspect, the present disclosure is directed to a kit for practicing the first or second assay method described above. The kit includes at least components (a)-(d). In some embodiments, the kit may further include a buffer, such as any of the buffers well known in the art and compatible with the assay methods, such as any of those described earlier above. The kit may or may not also include a pH adjuster (e.g., an acid and/or base) or disulfide reducing agent. The kit typically also includes directions for using the components to determine the level of activity of an acyl transferase enzyme or for determining the inhibition ability of a candidate compound.

In another aspect, the present disclosure is directed to compounds capable of inhibiting an acyl transferase enzyme, particularly a ZDHHC acyl transferase enzyme. The inhibitor compounds contain a fatty acyl portion, with halogen substitution at the alpha position. The halogen is typically selected from chlorine, bromine, and iodine. The inhibitor can be synthesized by methods well known in the art, as described in the Examples section of the present disclosure.

In some embodiments, the inhibitor compounds are within the scope of the following generic structure:

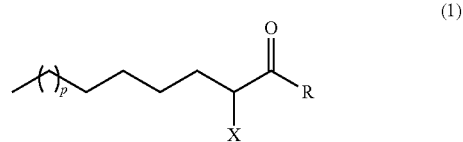

(1)

In Formula (1), R is a hydrocarbon group containing 2-12 carbon atoms and optionally containing one or more heteroatoms selected from oxygen, nitrogen, and sulfur, as described in detailed earlier above. R may be any of the types of hydrocarbon groups described above, such as a linear, branched, or cyclic alkyl or alkenyl group, or an aromatic or heteroaromatic group, any of which may or may not be substituted with one or more heteroatoms. The variable X is a halogen, such chlorine (Cl), bromine (Br), or iodine (I). In some embodiments, X is specifically bromine. The variable p is an integer of at least 1. In different embodiments, p is an integer of 1, 2, 3, 4, 5, 6, 7, 8, 9, 10, 11, 12, 13, 14, 15, 16, 17, 18, 19, or 20, or an integer within a range bounded by any two of the foregoing values, e.g., 1-20, 2-20, 3-20, 4-20, 5-20, 6-20, 7-20, 8-20, 9-20, 10-20, 1-5, 1-6, 1-7, 1-8, 1-9, 1-10, 1-11, 1-12, and 1-13.

In particular embodiments, the inhibitor compound has the following ketone structure in which R in Formula (1) is a hydrocarbon group ($R^a$):

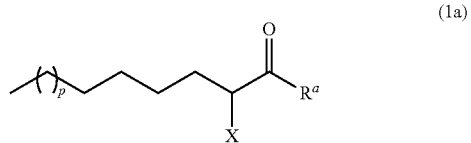

(1a)

In Formula (1a), $R^a$ is a hydrocarbon group containing 2-12 carbon atoms and composed of carbon and hydrogen atoms only. $R^a$ may be any of the types of hydrocarbon groups (R) described above, such as a linear, branched, or cyclic alkyl or alkenyl group, or an aromatic group, without heteroatom substitution. The variables X and p are as defined under Formula (1).

In other particular embodiments, the inhibitor compound has the following ester structure in which R in Formula (1) is $OR^1$:

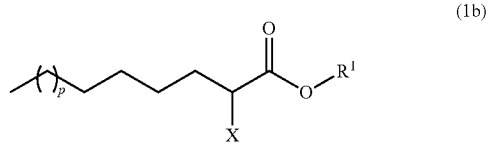

(1b)

In Formula (1b), $R^1$ is a hydrocarbon group (R) containing 2-12 carbon atoms and optionally containing one or more heteroatoms selected from oxygen, nitrogen, and sulfur, as described in detailed earlier above. $R^1$ may be any of the types of hydrocarbon groups described above, such as a linear, branched, or cyclic alkyl or alkenyl group, or an aromatic or heteroaromatic group, any of which may or may not be substituted with one or more heteroatoms. The variables X and p are as defined under Formula (1).

In other particular embodiments, the inhibitor compound has the following thioester structure in which R in Formula (1) is $SR^2$:

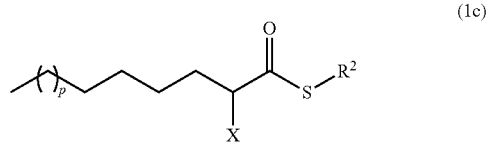

(1c)

In Formula (1c), $R^2$ is a hydrocarbon group (R) containing 2-12 carbon atoms and optionally containing one or more heteroatoms selected from oxygen, nitrogen, and sulfur, as described in detailed earlier above. $R^2$ may be any of the types of hydrocarbon groups described above, such as a linear, branched, or cyclic alkyl or alkenyl group, or an aromatic or heteroaromatic group, any of which may or may not be substituted with one or more heteroatoms. The variables X and p are as defined under Formula (1).

In particular embodiments, the compound of Formula (1c) has the following structure:

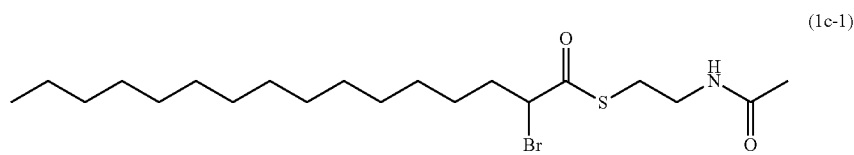 [SMILES: CCCCCCCCCCCCCCC(Br)C(=O)SCCNC(C)=O]

(1c-1)

In other particular embodiments, the inhibitor compound has the following amide structure in which R in Formula (1) is $NHR^3$:

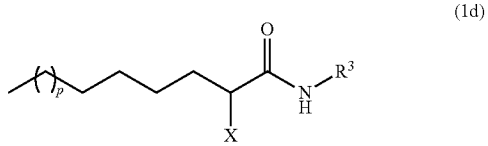

(1d)

In Formula (1d), $R^3$ is a hydrocarbon group (R) containing 2-12 carbon atoms and optionally containing one or more heteroatoms selected from oxygen, nitrogen, and sulfur, as described in detailed earlier above. $R^3$ may be any of the types of hydrocarbon groups described above, such as a linear, branched, or cyclic alkyl or alkenyl group, or an aromatic or heteroaromatic group, any of which may or may not be substituted with one or more heteroatoms. The variables X and p are as defined under Formula (1).

In particular embodiments, the compound of Formula (1d) has the following structure:

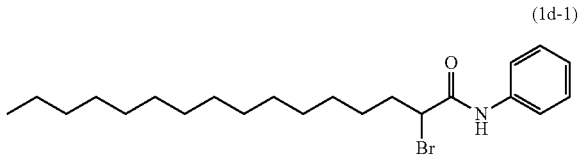 [SMILES: CCCCCCCCCCCCCCC(Br)C(=O)Nc1ccccc1]

(1d-1)

The inhibitor compounds considered herein have the ability to partially or completely inhibit acyl transferase activity. The ability of an inhibitor compound to inhibit acyl transferase activity is typically ascertained by measuring the $IC_{50}$ of the candidate compound. As used herein, "$IC_{50}$" or "50% inhibitory concentration" identifies how much of a compound is needed to inhibit activity by half. The $IC_{50}$ of a compound can be determined by constructing a dose-response curve and examining the effect of different concentrations of a compound on decreasing or preventing enzymatic activity. $IC_{50}$ values can be calculated for a given inhibitor by determining the concentration needed to inhibit half of the maximum enzymatic activity. The mathematical analysis used for deriving an $IC_{50}$ value is well known in the art. The inhibitors of the invention may inhibit acyl transferase activity with an $IC_{50}$ of, for example, up to or less than 1 µM, 2 µM, 5 µM, 10 µM, 20 µM, 30 µM, 40 µM, 50 µM, or 100 µM, or an $IC_{50}$ within a range bounded by any two of these values.

In some embodiments, the inhibitor compound is a selective inhibitor of an acyl transferase. A selective inhibitor of an acyl transferase may exhibit an $IC_{50}$ value against a specific type of acyl transferase that is lower than one or more other acyl transferases. For example, the inhibitor compound may exhibit an $IC_{50}$ value against ZDHHC3, ZDHHC7, or ZDHHC20 that is lower than one or more other ZDHHC enzymes or other acyl transferases in general.

In another aspect, the present disclosure is directed to a pharmaceutical composition that includes one or more of the inhibitor compounds described above dispersed in one or more physiologically acceptable carriers or excipients. The phrase "pharmaceutically acceptable excipient" or "pharmaceutically acceptable carrier", as used herein, refers to a pharmaceutically acceptable material, composition or vehicle, such as a liquid or solid filler, diluent, carrier, manufacturing aid (e.g., lubricant, talc magnesium, calcium or zinc stearate, or stearic acid), solvent or encapsulating material, useful for carrying or transporting the therapeutic composition for administration to the subject. Each excipient should be "acceptable" in the sense of being compatible with the other ingredients of the formulation and physiologically safe to the subject.

The pharmaceutical composition can also include one or more stabilizers, surfactants, salts, buffering agents, additives, or a combination thereof. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted and buffered.

The inhibitor compound in the pharmaceutical composition can also be a physiologically acceptable salt or solvate of any of the inhibitor compounds described above. Acceptable salts and solvates can be made by any of the techniques known in the art. As known in the art, a salt can be produced by reacting a basic portion (e.g., amino) of the active compound with a Bronsted acid, such as HCl or $H_2SO_4$, or with an electrophile, such as $CH_3Br$. If desired, the initially introduced anion or cation can be exchanged with another anion or cation. As also known in the art, a solvate can be produced by dissolving or otherwise treating the active compound with a solvent under conditions where one, two, or more solvent molecules remain associated with each molecule of the active ingredient.

Pharmaceutical compositions (including cosmetic preparations) may comprise from about 0.00001 to 100%, such as from 0.001 to 10% or from 0.1% to 5% by weight of one or more of the inhibitor compounds described herein. In topical formulations, the active agent may be present in an amount in the range of approximately 0.25 wt. % to 75 wt. % of the formulation, or in the range of approximately 0.25 wt. % to 30 wt. % of the formulation, or in the range of approximately 0.5 wt. % to 15 wt. % of the formulation, or in the range of approximately 1.0 wt. % to 10 wt. % of the formulation.

In another aspect, the invention is directed to methods for treating or preventing a disorder (i.e., disease or condition) whose etiology or expression is dependent on acyl transferase activity. The subject being treated is typically a human, although other mammals could possibly benefit. The methods include administering to a subject an acyl transferase inhibiting compound in a pharmaceutically effective amount, i.e., an amount that sufficiently inhibits acyl transferase activity to result in an effective treatment or prevention of the disorder. As used herein, the term "inhibitor" is a substance that at least partially decreases acyl transferase (or more specifically, ZDHHC) activity.

In one embodiment, the disease or condition being treated with the inhibitor compound is a neurodegenerative disease. The term "neurodegenerative disease", as used herein, generally refers to a disease that manifests as the progressive loss of neuronal function and structure. The neurodegenerative disease may be, for example, Parkinson's, Alzheimer's, or Huntington's Disease, amyotrophic lateral sclerosis (ALS), peripheral neuropathies, and other conditions characterized by damage, necrosis or loss of neurons, including for example central, peripheral, or motor neurons. In particular embodiments, the inhibitor compound being administered for treating a neurodegenerative disease is within the scope of Formula (1), (1a), (1b), (1c), or (1d), or a specific compound within any of these formulas.

In another embodiment, the disease or condition being treated with the inhibitor compound is cancer, which may be in the form of a neoplasm. The cancer can be located in any part of the body. Some examples of applicable body parts containing cancer cells include the breasts, lungs, stomach, intestines, prostate, ovaries, cervix, pancreas, kidney, liver, skin, lymphs, bones, bladder, uterus, colon, rectum, or brain. The cancer can also include the presence of one or more carcinomas, sarcomas, lymphomas, blastomas, or teratomas (germ cell tumors). The cancer may also be a form of leukemia. In some embodiments, the cancer is a triple negative breast cancer. In particular embodiments, the inhibitor compound being administered for treating cancer is within the scope of Formula (1), (1a), (1b), (1c), or (1d), or a specific compound within any of these formulas.

In yet other embodiments, the disease or condition being treated with the inhibitor compound is diabetes, obesity, cardiovascular disease (e.g., atherosclerosis), a blood clotting disorder, or an inflammatory disorder or condition (e.g., rheumatoid arthritis). The diabetes can be, for example, a type 1 or 2 diabetes, pre-diabetes, or a related or at-risk condition, such as hypoglycemia. In some embodiments, the inhibitor compound functions to normalize or maintain blood sugar level or insulin level or function. In other embodiments, the inhibitor compound functions to treat or prevent a diabetic complication, such as renal failure, cardiovascular disease, retinopathy, neuropathy, ketoacidosis, or fatty liver disease.

The data obtained from cell culture assays and animal studies can be used in formulating a range of dosage for use in humans. The dosage of such compounds may lie within a range of circulating concentrations that include the $IC_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

As is well known in the art, the dosage of the active ingredient(s) generally further depends on the disorder or condition being treated, the extent of the disorder or condition, the method of administration, size of the patient, and potential side effects. In different embodiments, depending on these and other factors, a suitable dosage of the inhibitor compound and/or other active ingredient may be precisely, at least, above, up to, or less than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

In certain embodiments, the inhibitor compound described herein may be taken alone, while in other embodiments it may be taken in combination with one or more other compounds that may or may not also function to inhibit or favorably augment or modify the activity of the inhibitor compound. In one embodiment, a mixture of two or more inhibitor compounds may be administered to a subject in need thereof. In another embodiment, one or more inhibitor compounds may be administered with one or more therapeutic agents for the treatment or prevention of a disorder whose etiology or expression is dependent, at least to some extent, on acyl transferase activity. In some embodiments, the one or more therapeutic agents are administered at the same time as the inhibitor compound (e.g., as a pharmaceutical composition containing the one or more therapeutic agents and inhibitor compound), while in another embodiment, the one or more therapeutic agents are administered separately from the inhibitor compound. When using separate formulations, the inhibitor compound may be administered at the same time, prior to, subsequent to, or intermittently or staggered with the administration of another therapeutic agent.

The inhibitor compounds and their physiologically acceptable salts and solvates may be administered (and suitably formulated therefore) by, for example, injection (e.g. SubQ, IM, IP, IV), inhalation or insufflation (either through the mouth or the nose) or oral, buccal, sublingual, transdermal, nasal, parenteral or rectal administration. In some embodiments, an inhibitor compound may be administered locally, at the site where the target cells are present, i.e., in a specific tissue, organ, or fluid (e.g., blood, cerebrospinal fluid, etc.). The inhibitor compounds can be formulated for a variety of modes of administration, including systemic, topical, or localized administration. Techniques of administration and the design of formulations are well known in the art, such as described in, for example, Remington's Pharmaceutical Sciences, Meade Publishing Co., Easton, Pa.

Examples have been set forth below for the purpose of illustration and to describe the best mode of the invention at the present time. However, the scope of this invention is not to be in any way limited by the examples set forth herein.

EXAMPLES

Herein is reported a simple mix-and-measure high-throughput assay for ZDHHCs using the acylation-coupled lipophilic induction of polarization (Acyl-cLIP) method (Lanyon-Hogg et al., Chem. Sci., 10, 8995-9000, 2019). In this assay, the ZDHHC peptide substrate is fluorescently labeled and the acylation triggers the binding of the fluorescent peptide to detergent micelles, increasing the fluorescent polarization. The process is schematically depicted in FIG. 1. Thus, the level of fluorescent polarization is the read out of ZDHHC enzyme activity. In this assay, the experiments can be performed in an all-in-one format with comparatively low cost and background signal. The following work demonstrates that the Acyl-cLIP assay was successful for determining activity of ZDHHC3, 7, and 20. Moreover, several 2-bromopalmitate (2-BP) analogs were evaluated as ZDHHC inhibitors using this method.
Results and Discussion To establish an acyl-cLIP assay for ZDHHCs, a peptide substrate was first selected. As several ZDHHCs palmitoylate Ras family proteins, a 15-mer peptide sequence from KRas4a, ISKEEKTPGCVKIKK (SEQ ID NO: 1), was selected as the ZDHHC substrate peptide. Previous Ras palmitoylation assays used a farnesylated Ras peptide as it is generally believed that farnesylation is important for recognition by ZDHHCs. However, the farnesylated peptide is difficult to make and is not commercially available. Furthermore, the farnesylated peptide would not be compatible with the acyl-cLIP assay because farnesylation would facilitate partitioning of the peptide in detergent micelles. To develop a simple assay that can be easily implemented, the experiments first tested whether the KRas4a peptide without farnesylation can be used by ZDHHCs as a substrate. ZDHHC-catalyzed S-palmitoylation was detected by LC-MS. To facilitate detection by UV, two tryptophan residues were added to the C-terminus of the peptide. In a second peptide, the 5-FAM group was attached to permit detection in the acyl-cLIP assay. Notably, palmitoylation of both KRas4a peptides was detected in the reactions containing ZDHHC7, but not in the control reaction without ZDHHC7. Next experiments measured enzyme kinetics of ZDHHC7 on the FAM-KRas4a peptide using high performance liquid chromatography (HPLC). The measured $K_m$ and $k_{cat}$ were 184 uM and 0.271 $s^{-1}$, respectively, and the calculated $k_{cat}/K_m$ value was $1.47 \times 10^3$ $M^{-1}s^{-1}$. Thus, the KRas4a peptide without farnesyla-tion is a respectable substrate for ZDHHC7 and suitable for the Acyl-cLIP assay.

Next experiments tested the FAM-KRas4a peptide in the Acyl-cLIP assay. Following the protocol from the previously reported Acyl-cLIP assay, 0.1% n-dodecyl-β-D-maltoside (DDM) in water was prepared to form micelles. To the solution of DDM in water, MES buffer (pH 6.4), TCEP, and palmitoyl-CoA were added. FAM-KRas4a peptide was then added to the reaction mixture, followed by ZDHHC enzyme to initiate the assay.

Figures 2A, 2B, 2C:
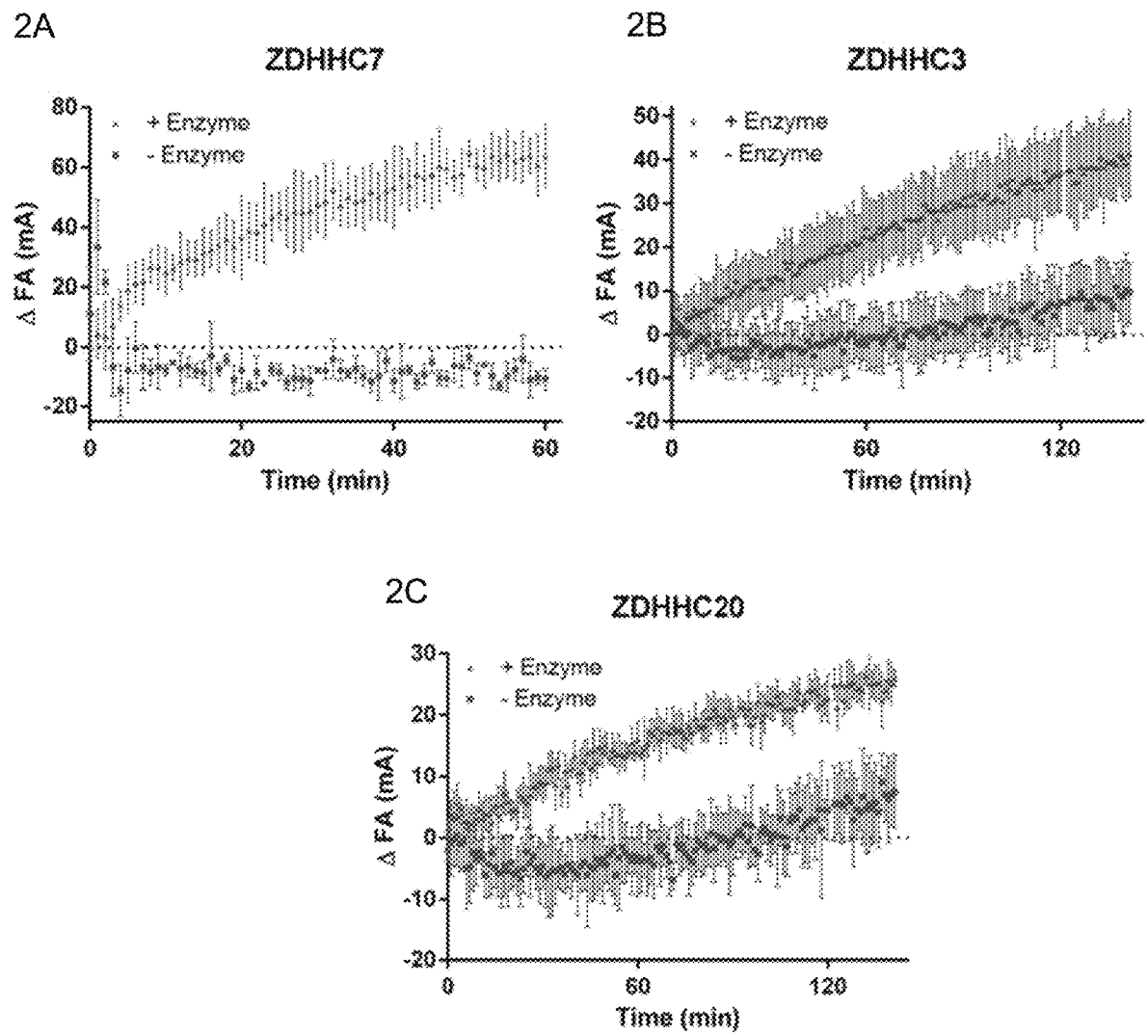
FIGS. 2A-2C. Real-time monitoring of FAM-KRas4a peptide palmitoylation by ZDHHC7/3/20.

In the presence of the FAM-KRas4a peptide and ZDHHC7, a time-dependent increase was observed in fluorescence anisotropy in one hour, as demonstrated by the results provided in FIGS. 2A-2C. No increase was observed for the samples without ZDHHC7 (FIGS. 2A-2C). These results clearly demonstrate ZDHHC7-dependent palmitoylation and successful binding of the fatty acylated FAM peptide to DDM micelles. Similar trends were also observed for ZDHHC3 and ZDHHC20 (FIGS. 2A-2C). However, these two enzymes showed weaker activities toward the peptide substrate compared to ZDHHC7. Thus, fluorescence anisotropy was observed for a longer time, which also led to a slight increase in fluorescence anisotropy of the samples without enzyme. This is likely due to non-enzymatic acylation. Nevertheless, a faster increase of the signal was detected with ZDHHC3 or ZDHHC20, suggesting that this assay could also be used to detect the activity of these enzymes.

To accommodate a high-throughput screening for small molecule ZDHHC inhibitors, a stopped-time assay was performed using the Acyl-cLIP method. Based on the real-time monitoring of ZDHHC7 and ZDHHC3, 30 minutes was selected for ZDHHC7 and 1 hour for ZDHHC3 for the stopped-time assay to match the initial linear reaction rate. After 30 minutes of ZDHHC7- and 60 minutes of ZDHHC3-catalyzed acylation, the reaction was quenched by adding an excess amount of K-Ras4a peptide without FAM. The stability of the fluorescence anisotropy signal was then monitored over 30 minutes and it was found that the signal was stable within a 30-minute period. For ZDHHC7, the signal-to-noise was 21.1, and Z'-factor was 0.553. For ZDHHC3, the signal-to-noise was 15.5, and Z'-factor was 0.594. Overall, these values indicate that a ZDHHC3/7 Acyl-cLIP assay is suitable for high-throughput screening.

Figure 3:
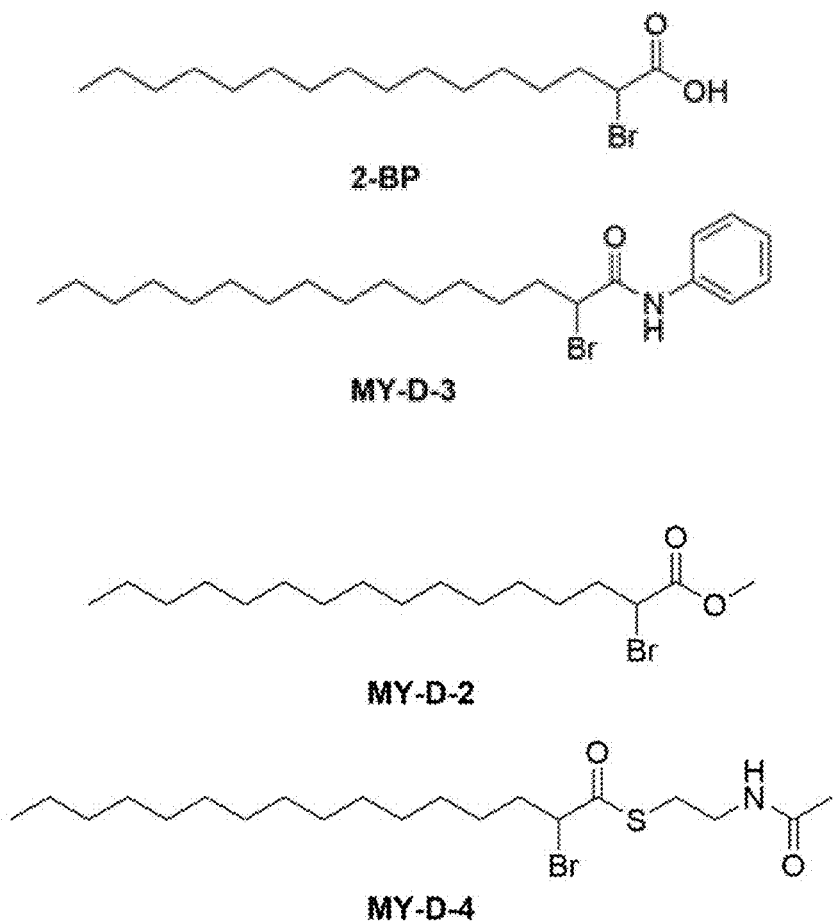
FIG. 3 shows chemical structures of some inhibitor compounds.

Next experiments tested whether the Acyl-cLIP assay can be used to detect ZDHHC inhibitors. The most commonly used inhibitor is 2-BP. To facilitate the evaluation of the Acyl-cLIP assay, several analogs of 2-BP were synthesized with different in vitro inhibition potency. 2-BP forms a covalent bond with the cysteine of the DHHC motif on its a-position carbon (B. C. Jennings et al., *J. Lipid Res.*, 50, 233-242, 2009). Thus, it was hypothesized that the attachment of a more electron-deficient carbonyl group, instead of carboxylic acid, would increase reactivity of the α-carbon, thereby increasing the inhibition potency, while the more electron-rich carbonyl group would decrease the potency. With this rationale in mind, three compounds were designed: an ester (MY-D-2), an amide (MY-D-3), and a thio-ester (MY-D-4). The structures of these compounds are shown in FIG. 3.

TABLE 1

$IC_{50}$ values of 2-BP, MY-D-2, MY-D-3, and MY-D-4 measured using different assays.

| $IC_{50}$ (μM) | ZDHHC7 (Acyl-cLIP)* | ZDHHC7 (MyrGia)** | ZDHHC3 (Acyl-cLIP)* |
|---|---|---|---|
| 2-BP | 9.0 ± 1.2 | 16 ± 1.3 | >250 |
| MY-D-2 | 38 ± 1.8 | 29 ± 1.3 | No Inhibition |
| MY-D-3 | >150 | 78 ± 1.4 | No Inhibition |
| MY-D-4 | 4.4 ± 1.8 | 1.6 ± 1.0 | ~50 |

Using the Acyl-cLIP assay, the $IC_{50}$ of these four inhibitors were measured against ZDHHC7 and ZDHHC3. Because these inhibitors may form irreversible covalent bonds with ZDHHCs, the order of adding the reagents were changed and included a 30-minute pre-incubation time to permit the bond to form prior to the addition of the FAM peptide and palmitoyl-CoA to initiate the reaction. For ZDHHC7, the $IC_{50}$ values of 2-BP, MY-D-2, and MY-D-4 were 9.0, 38, and 4.4 μM, respectively (Table 1), while MY-D-3 showed no inhibition even at 150 μM. Without the pre-incubation, $IC_{50}$ values of 2-BP, MY-D-2, and MY-D-4 were 12, 75, and 6.3 μM, respectively, which are slightly higher than with pre-incubation. MY-D-2, which contains a methyl ester, showed a slightly weaker potency than 2-BP. Meanwhile, MY-D-3, which contains an electron-rich amide, did not inhibit ZDHHC7. MY-D-4, which contains a more electron-deficient thioester, inhibited ZDHHC7 slightly stronger than 2-BP.

To further evaluate the potency of the inhibitors, the four compounds were tested using ZDHHC7-catalyzed palmitoylation of myristoylated (myr) Gi protein a subunit (Gia) using an established in vitro assay with [$^3$H]palmitoyl-CoA. Myr-Gia was previously reported as a substrate for ZDHHC7 (R. Tsutsumi et al., *Mol. Cell. Biol.*, 29, 435-447, 2009). ZDHHC7 and the inhibitors were pre-incubated at 30° C. for 10 min, followed by the addition of [$^3$H]palmitoyl-CoA and myr-Gia. The acylation reaction was allowed to proceed at 30° C. for 10 min, the reaction was quenched, and the proteins resolved by SDS-PAGE. The [$^3$H]-palmitoylated myrGia band was excised from the gel and the level of [$^3$H]palmitoylation was measured by scintillation counting. Using this assay, the measured ZDHHC7 $IC_{50}$ values of 2-BP, MY-D-2, MY-D-3, and MY-D-4 were 16, 29, 78 and 1.6 μM, respectively (Table I). Analogous to what was found in the acyl-cLIP assay, MY-D-4 showed the strongest inhibition towards ZDHHC7. Additionally, MY-D-2 and MY-D-3 inhibited ZDHHC7 weaker than 2-BP. Overall, the order of inhibition of the four compounds in the established assay with myrGia as a substrate was the same as that observed with the Acyl-cLIP assay using a peptide substrate, all of which further demonstrates the utility of the Acyl-cLIP method.

In addition to ZDHHC7, the $IC_{50}$ values of 2-BP and MY-D-4 were also measured against ZDHHC3 using the Acyl-cLIP. The DHHC3 $IC_{50}$ value for 2-BP and MY-D-4 were approximately 250 and 50 μM, respectively (Table 1). In accordance with the previous ZDHHC7 assays, MY-D-4 showed stronger inhibition than 2-BP. Interestingly, both compounds inhibited ZDHHC3 much less than ZDHHC7, demonstrating that 2-BP might display some selectivity among the 23 ZDHHCs.

The results of the Acyl-cLIP assay were also compared with a conventional assay using HRas protein. Next experiments screened at a fixed inhibitor concentration of 1 μM against ZDHHC3 and ZDHHC7 using [$^3$H]palmitoyl-CoA and HRas protein as substrates. The levels of [$^3$H]palmitoylated HRas were detected. For both ZDHHC3 and ZDHHC7, MY-D-4 showed the strongest inhibition among the four compounds, followed by 2-BP, MY-D-2, and MY-D-3. These results further confirmed the inhibition trends from the previous assays.

Figure 4A:
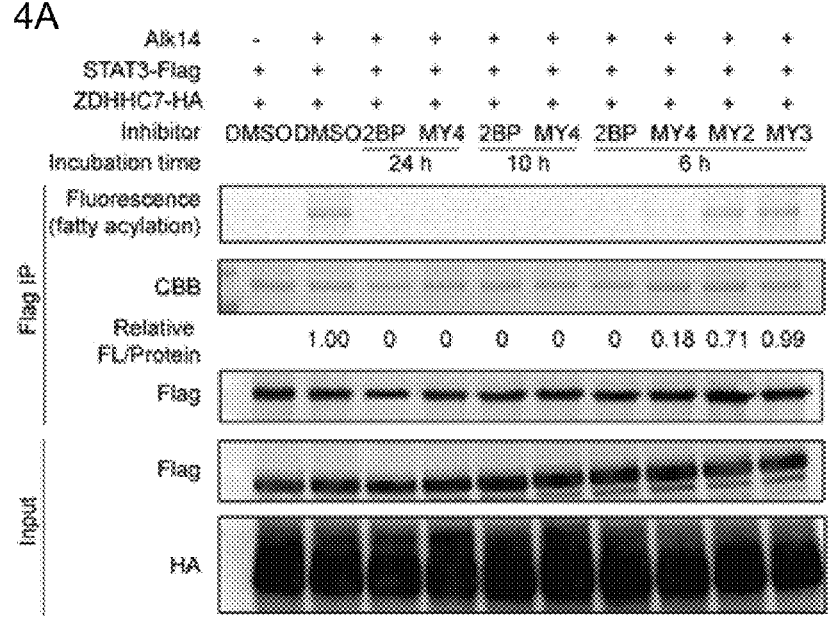
FIGS. 4A-4B. The results show that MY-D-4 inhibits ZDHHC3 and 7 in living cells.

Next experiments tested whether the four compounds could also inhibit ZDHHC7 in cells. ZDHHC7 was recently reported to palmitoylate STAT3 (M. Zhang et al., Nature, 586, 434-439, 2020). Flag-tagged STAT3 and HA-tagged ZDHHC7 were expressed in HEK293T cells. The cells were incubated with the four inhibitors. During the last six hours of the incubation, 50 μM of Alk14 probe was added to metabolically label palmitoylated STAT3. After collecting and lysing the cells, STAT3 was immunoprecipitated and the levels of acylation were determined by in-gel fluorescence after click chemistry. With a 6-hour inhibitor treatment, STAT3 acylation was abolished by 50 μM 2-BP. MY-D-4 at a concentration of 50 μM also significantly reduced STAT3 fatty acylation, but the effect appeared to be slightly weaker than that with 2-BP. The foregoing results are evidenced in FIG. 4A. By contrast, MY-D-2 only slightly decreased fatty acylation and MY-D-3 had no effect. With 12- and 24-hour inhibitor treatment, both 2-BP and MY-D-4 completely eliminated STAT3 acylation (FIG. 4A). A time-dependent inhibition assay was also conducted with 25 µM of 2-BP and MY-D-4. Again, a similar trend was obtained, with 2-BP slightly more inhibitory effect than MY-D-4. With a fixed 6-hour inhibitor treatment, 2-BP and MY-D-4 were also compared at different concentrations. Similar concentration-dependent inhibition of STAT3 acylation was observed with 2-BP and MY-D-4 with $IC_{50}$ values between 1 and 5 µM. Based on these results, in-cell inhibition of ZDHHC7 by MY-D-2 and MY-D-3 aligned well with the in vitro assay results, with MY-D-2 showing only mild inhibition and MY-D-3 showing no inhibition of ZDHHC7. However, MY-D-4, which was predicted to be a slightly stronger inhibitor than 2-BP, showed slightly weaker than or similar potency to 2-BP in cells. One possible explanation for why 2-BP is weaker in vitro but stronger in cells is that it can be converted to 2-BP-CoA, which could be a much more potent inhibitor of ZDHHC enzyme activity.

Figure 4B:
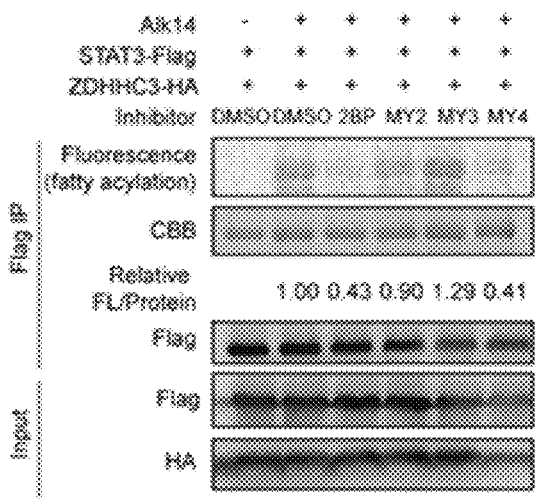

Next experiments also tested the four compounds for ZDHHC3 inhibition in HEK293T cells that over-express both ZDHHC3 and STAT3. Like the trend observed with ZDHHC7, a 6-hour treatment with 25 µM 2-BP and MY-D-4 decreased ZDHHC3-catalyzed STAT3 acylation by more than 50%, while MY-D-2 only slightly affected, and MY-D-3 did not alter the acylation level of STAT3. Notably, the inhibition of zDHHC3 by 2-BP and MY-D-4 is weaker than that of ZDHHC7 (comparing FIG. 4B with ZDHHC3, 25 µM inhibitors, 6-hour treatment versus with ZDHHC7, 25 µM inhibitors and 6-hour treatment). This result is again consistent with the acyl-cLIP assay showing stronger inhibition of ZDHHC7 than ZDHHC3 by 2-BP and MY-D-4. Thus, the results from the Acyl-cLIP assay can be used to predict cellular responses.

General methods. Chemical reagents and organic solvents that were used in this disclosure were analytical or higher grades, and acquired from commercial vendors. FAM-Kras peptide with sequence of ISKEEKTPGCVKIKK (SEQ ID NO: 1) with N-terminal 5-carboxyfluorescein (5-FAM) group and non-FAM KRas peptide with the identical sequence without the N-terminal 5-FAM group were purchased from Biomatik. 2-Bromopalmitate used in disclosure was obtained from a commercial source.

Unless specifically noted, all chemical reaction took place under nitrogen gas. SiliaFlash Irregular Silica Gel P60, 40-63 µM, 60 Å was used for silica gel column purification. After the purification, the overall purities of all the final compounds were confirmed to be >95% by Shimadzu HPLC 20-AD. Collected NMR spectra were performed on a Bruker 500. The mass detection was performed on a Shimadzu HPLC LC20-AD and Thermo Scientific LCQ Fleet Mass Spectrometer (positive ion mode), using HPLC-grade water with 0.1% HPLC-grade acetic acid as buffer A and HPLC-grade acetonitrile with 0.1% HPLC-grade acetic acid as buffer B. The column used was Kinetex 5u EVO C18 100 Å Column (30×2.1 mm, 5 µM), and the UV detection wavelengths were 215 and 260 nm. For the HPLC DHHC assays, Shimadzu HPLC LC20-AD with HPLC-grade water with 0.1% trifluoroacetic acid as buffer A and HPLC-grade acetonitrile with 0.1% trifluoroacetic acid as buffer B was used. To this setup, Kinetex 5u EVO C18 100 Å column (100 mm×4.60 mm, 5 µm) was attached.

Cell culture methods. HEK 293T cells from ATCC were cultured in Dulbecco's Modified Eagle Medium (11965-092, Gibco) supplemented with 10% bovine calf serum (12133C, Sigma). Cells were incubated at 37° C. with 5% $CO_2$.

Immunoblots. Immunoblots were done by known methods. Cells were lysed by 1% NP-40 lysis buffer (25 mM Tris-HCl pH 8.0, 10% glycerol, 150 mM NaCl, 1% Nonidet P-40) with protease inhibitor cocktail (P8340, Sigma). Signals were detected using the chemiluminescence of ECL plus (32132, Thermo Fisher) on the Typhoon 7000 Variable Mode Imager (GE Healthcare Life Sciences).

ZDHHC3/7/20 Acyl-cLIP Assay (Real-Time Monitoring).

n-Dodecyl β-D-maltoside (DDM, 1.3 mg) was dissolved in 1 mL of water by vigorous vortexing. Preparing for 19 samples, "Buffer A" was prepared as follows: In a 1.5 mL Eppendorf tube with the DDM solution (190 µL), MES buffer pH 6.5 (stock concentration 500 mM, 38 µL), TCEP (stock concentration 30 mM, 6.33 µL), palmitoyl-CoA (stock concentration 1.5 mM, 12.6 µL) and FAM-KRas4a substrate (stock concentration 0.5 mM, 19 µL) were added. For the same 19 samples, "Buffer B" was prepared as followed. In a 1.5 mL Eppendorf tube with the DDM solution (95 µL), ZDHHC7 (stock concentration 6 µM, 19 µL) was added. To each well of a black 384 well plate (Corning 3575), 14 µL of "Buffer A" was added. Then, 6 µL of "Buffer B" was added to initiate the reaction. The final concentration of the reaction mixture was 50 mM MES pH 6.4, 0.5 mM TCEP, 40 µM palmitoyl-CoA, 0.3 µM ZDHHC7, and 25 µM FAM-KRas4a substrate in 0.1% DDM solution. The volume of the components can vary depending on the activity of the purified enzyme and sample number. The real-time fluorescence anisotropy was measured with "8040561 Filter BLK ASBY GRN FP VSBL K" cube at excitation of 485/20 nm, emission of 528/20 nm, and normal read speed mode. The measurements were done in 8 replicates.

ZDHHC3 and ZDHHC20 were analyzed at 0.6 µM, using a similar protocol.

For 19 samples, "Buffer A" was prepared as follows: In a 1.5 mL Eppendorf tube with the DDM solution (133 µL), MES buffer pH 6.5 (stock concentration 500 mM, 38 µL), TCEP (stock concentration 30 mM, 6.33 µL), palmitoyl-CoA (stock concentration 1.5 mM, 12.6 µL) and FAM-KRas4a substrate (stock concentration 0.5 mM, 19 µL) were added. For the same 19 samples, "Buffer B" was prepared as followed. In a 1.5 mL Eppendorf tube with the DDM solution (95 µL), ZDHHC3/20 (stock concentration 3 µM, 76 µL) was added. To each well of a black 384 well plate (Corning 3575), 11 µL of "Buffer A" was added. Then, 9 µL of "Buffer B" was added to initiate the reaction. The rest of the experiment was done identical to the ZDHHC7 assay.

ZDHHC7 Acyl-cLIP Assay (End-Point Method).

n-Dodecyl β-D-maltoside (DDM, 1.3 mg) was dissolved in 1 mL of water by vigorous vortexing. Preparing for 19 samples, "Buffer A" was prepared as follows: In a 1.5 mL Eppendorf tube with the DDM solution (190 µL), MES buffer pH 6.5 (stock concentration 500 mM, 38 µL), TCEP (stock concentration 30 mM, 6.33 µL), and ZDHHC7 (stock concentration 6 µM, 19 µL) were added. For the same 19 samples, "Buffer B" was prepared as followed. In a 1.5 mL Eppendorf tube with the DDM solution (76 µL), palmitoyl-CoA (stock concentration 1.5 mM, 12.6 µL) and FAM-Kras4a substrate (stock concentration 0.5 mM, 19 µL) was added. To each well of a black 384 well plate (Corning 3575), 1 µL of inhibitor (concentration ranging from 93.75 µM to 6000 µM) was added. First, 13.3 µL of "Buffer A" was added to each well. After a 30-minute pre-incubation, 5.66 µL of "Buffer B" was added. The final concentration of the reaction mixture was 50 mM MES pH 6.4, 0.5 mM TCEP, 40 µM palmitoyl-CoA, 0.3 µM ZDHHC7, and 25 µM FAM-KRas4a substrate in 0.1% DDM solution. After 30 minutes, the reaction was quenched by adding 4 µL of 6 mM non-FAM KRas-4a substrate. The fluorescence anisotropy was measured by citation 5 with "8040561 Filter BLK ASBY GRN FP VSBL K" cube at excitation of 485/20 nm, emission of 528/20 nm, and normal read speed mode. The measurements were done in 3 replicates at each inhibitor concentration.

ZDHHC3 was assayed using the similar protocol at a final concentration of 0.6 µM.

Preparing for 19 samples, "Buffer A" was prepared as follows: In a 1.5 mL Eppendorf tube with the DDM solution (133 µL), MES buffer pH 6.5 (stock concentration 500 mM, 38 µL), TCEP (stock concentration 30 mM, 6.33 µL), and ZDHHC3 (stock concentration 6 µM, 76 µL) were added. For the same 19 samples, "Buffer B" was prepared as followed. In a 1.5 mL Eppendorf tube with the DDM solution (76 µL), palmitoyl-CoA (stock concentration 1.5 mM, 12.6 µL) and FAM-KRAS4a substrate (stock concentration 0.5 mM, 19 µL) was added. To each well of a black 384 well plate (Corning 3575), 1 µL of inhibitor (concentration ranging from 93.75 µM to 6000 µM) was added. First, 13.3 µL of "Buffer A" was added to each well. After a 30-minute pre-incubation, 5.66 µL of "Buffer B" was added. The rest of the experiment was done identical to the ZDHHC7 assay.

Detection of ZDHHC acylated FAM peptide by LC-MS. In a solution containing 0.1% DDM, 50 mM MES pH 6.4, 0.5 mM TCEP, 300 nM DHHC7 and 60 µM palmitoyl-CoA, the FAM-KRas4a peptide was added to a final concentration of 50 µM. The reaction was then incubated at 37° C. for 1 hour. After quenching the reaction with 1% acetonitrile, the mixture was centrifuged at 17 000 g for 10 minutes. The supernatant was then analyzed using LC-MS to detect the acylated FAM peptide. For the HPLC DHHC assays, Shimadzu HPLC LC20-AD with HPLC-grade water with 0.1% trifluoroacetic acid as buffer A and HPLC-grade acetonitrile with 0.1% trifluoroacetic acid as buffer B was used. To this setup, Kinetex 5u EVO C18 100 Å column (100 mm×4.60 mm, 5 µm) was attached. At a constant flow rate of 0.3 mL/min, the linear gradient for the analysis was 0% Buffer B (0-2 min), 10% Buffer B (2-4 min), 100% Buffer B (4-10 min), 100% Buffer (10-13.90 min), 0% Buffer B (13.90-14 min), and 0% Buffer B (14-15 min). The peaks were observed under UV absorbance at 215 and 260 nm and a positive-ion mode.

Measurement of $K_m$ and $k_{cat}$ of FAM-Kras4a peptide. In solutions containing 0.1% DMM, 50 mM MES pH 6.4, 0.5 mM TCEP, 60 µM palmitoyl-CoA, and 0.15 µM DHHC7, FAM-KRas peptide was added to final concentration ranging from 31.25 µM to 2000 µM. After 10 minutes of incubation, the reaction was quenched with 0.1% acetonitrile. After centrifuging at 17 000 g for 10 minutes, the supernatant was loaded to Shimadzu HPLC LC20 Ad with Kinetex 5u EVO C18 100 Å column (100 mm×4.60 mm, 5 µm) for UV detection at 260 nm. Using HPLC-grade water with 0.1% trifluoroacetic acid as Buffer A and HPLC-grade acetonitrile with 0.1% trifluoroacetic acid, at a constant rate of 0.5 mL/min, the linear gradient for elution was 0% Buffer B (0-2 min), 20% Buffer B (2-4 min), 40% Buffer B (4-17 min), 100% Buffer B (17-19 min), 100% Buffer B (19-24 min), 0% Buffer B (24-25 min), and 0% Buffer B (25-30 min). Product formed was quantified using the ratio of substrate and product peak areas. After the detection, $K_m$ and $k_{cat}$ values were measured by GraphPad Prism software.

Purification of ZDHHC enzymes. The following purified ZDHHC enzymes were used in this study: mouse ZDHHC3-FLAGHis, mouse ZDHHC7-mycHis, human ZDHHC9-Strep: human GCP16-Strep complex, and frog ZDHHC20-Strep.

Recombinant baculovirus encoding ZDHHC3 was generated by cloning a ZDHHC3 cDNA that includes a C-terminal FLAG epitope and His tag into a pFastBac1 vector. ZDHHC7 was made by cloning ZDHHC7 cDNA into a pblueBac4.5-myc3His10 to include a C-terminal myc and His tag. ZDHHC9 was generated by cloning the cDNA into pCNG-FB7 vector to include a C-terminal STREP tag. A GCP16 baculovirus was generated similarly. ZDHHC20 was made by cloning the ZDHHC20 cDNA into pCGFP-FB3 vectors to include a C-terminal Strep tag. All constructs were expressed in Sf9 insect cells and infected at 2.5-4.0×10^6 cells/mL with the appropriate ZDHHC baculovirus. Infected cells were incubated at 27° C. for 48 h, except for ZDHHC9- and GCP16-infected cells, which were incubated at 27° C. for 24 h, followed by incubation at 18° C. for an additional 48 h. Cells were harvested by centrifugation at 500×g and then washed twice with ice-cold PBS and flash frozen until purification.

Purification of ZDHHC3-FLAGhis was done as previously described following a two-step affinity purification using Ni-NTA resin followed by a FLAG resin. For ZDHHC7-mycHis, purification was done using a Ni-NTA resin.

For the purification of the ZDHHC9:GCP16 protein complex, cells infected with equal amounts of ZDHHC9-STREP and GCP16-STREP viruses were pelleted and washed twice with ice-cold PBS. Cells were then disrupted in lysis buffer (PBS, 1% dodecylmaltoside (DDM), 15% glycerol, 0.5 mM TCEP and protease inhibitors (0.5 µg/mL leupeptin, 3 µg/mL aprotinin, 0.3 µg/mL pepstatin A, and 0.5 mM phenylmethylsulfonyl fluoride)). The lysate was centrifuged at 3,100×g for 10 min at 4° C. to remove cell debris and the supernatant was centrifuged again at 100,000×g for 45 min at 4° C. The soluble fraction was incubated with Streptactin Sepharose High Performance resin (GE Healthcare) for 2 h by batch method. The resin was pelleted by centrifugation and transferred to a gravity column (Bio Rad) and washed with 10× column volume of wash buffer (PBS, 15% glycerol, 0.5 mM TCEP, 0.5 mM DDM). The ZDHHC9:GCP16 protein complex was then eluted in Strep elution buffer (100 mM Tris HCl (pH 8.0), 150 mM NaCl, 1 mM EDTA, 15% glycerol, 0.5 mM DDM and 0.5 mM TCEP). Size exclusion chromatography (SEC) of pooled Strep fractions was done to resolve the ZDHHC9:GCP16 complex from free ZDHHC9 and GCP16 using a Superdex 200 (GE Healthcare) in SEC buffer (20 mM HEPES (pH 7.4), 150 mM NaCl, 0.5 mM TCEP, 15% glycerol, and 0.5 mM DDM). Fractions containing the ZDHHC9:GCP16 complex were pooled and used in the in vitro assays.

The procedure for purifying ZDHHC20-STREP was similar to that of the ZDHHC9:GCP16 complex, except that the lysis buffer, wash buffer, and elution buffer contained 10% glycerol. Additionally, the Strep tag in ZDHHC20 was removed by incubation with thrombin enzyme (1:100) for 12 h at 4° C. Purified ZDHHC20 was separated from thrombin by SEC using the same SEC buffer described above, except with 50 mM Tris (pH 7.4).

The ZDHHC9:GCP16 protein concentration was determined by measuring A280 of the complex using Nanodrop. The concentrations of the other ZDHHC proteins were determined by plotting elution samples along a linear curve generated with known concentrations of bovine serum albumin stained with Coomassie gel stain and quantified using a VersaDoc™ 5000 imaging system.

ZDHHC7-myrGia PAT Assay. Rat Myr-Gia was generated by transforming C-terminally His-tagged Gia in JM101 competent cells containing the N-myristoyltransferase (NMT) plasmid. Following inoculation and induction of the bacterial cells, myr-Gia was purified from total cell lysates using Ni-NTA resin. To assess the inhibition of ZDHHC7-mediated myr-Gia palmitoylation, equal volumes of purified ZDHHC7 enzyme (100 nM) and inhibitors (0-100 µM) were incubated for 10 min at 30° C. The PAT reaction was then initiated by mixing the enzyme:inhibitor solution with [$^3$H]-palmitoyl CoA (1 µM) and myr-Gia (1 µM). The reaction was allowed to proceed for 10 min at 30° C. and then stopped with the addition of sample buffer containing 10 mM TCEP. Proteins were resolved on a Coomassie-stained gel, and the myr-Gia band was excised and dissolved in Soluene (Perkin-Elmer). The excised bands were heated at 37° C. overnight and then combined with Ultima Gold scintillation fluid (Perkin-Elmer). Radioactivity was measured by scintillation counting. $IC_{50}$ values for the inhibitors were calculated by plotting the inhibition curves in GraphPad Prism.

ZDHHC-HRas PAT Assay. His-HRas was purified from total cell lysates of baculovirus-infected Sf9 cells using Ni-NTA resin. A similar PAT assay for assessing the inhibition of ZDHHC-mediated HRas palmitoylation was performed as described above except that the purified ZDHHC enzyme concentration was 50 nM and a single concentration of inhibitor (1 µM) was used.

Detection of ZDHHC3/7 inhibition by monitoring STAT3 fatty acylation. HEK 293T cells were transfected with STAT3-Flag and ZDHHC3-HA or ZDHHC7-HA for 36 h, and treated with 50 µM 2-BP, MY-D-2, MY-D-3, or MY-D-4 for the indicated time with 6 h Alk14 labeling (50 µM). Cells were collected and lysed in the 1% NP-40 lysis buffer (25 mM Tris-HCl pH 8.0, 10% glycerol, 150 mM NaCl, 1% Nonidet P-40) with protease inhibitor cocktail (P8340, Sigma). STAT3-Flag was purified by anti-Flag agarose beads and resuspended in 50 µL IP wash buffer (25 mM Tris-HCl pH 8.0, 150 mM NaCl, 0.2% Nonidet P-40). Click chemistry was done by adding a mixture of 3 µL of 2 mM TAMRA azide (47130, Lumiprobe), 3.6 µL of 10 mM tris[(1-benzyl-1H-1,2,3-triazol-4-yl)methyl]amine (TBTA) (T2993, TCI chemicals), 3 µL of 40 mM CuSO4, 3 µL of 40 mM tris(2-carboxyethyl)phosphine HCl (TCEP hydrochloride) (580560, Millipore) to each sample. The mixtures were mixed by vortex and incubated in dark at room temperature for 30 min. 20 µL of the 6x loading buffer was added into each reaction mixture and the mixture was boiled at 95° C. for 10 min to denature. The mixture was separated by SDS-PAGE gel. The gel was scanned by the Typhoon 7000 Variable Mode Imager (GE Healthcare Life Sciences) in the rhodamine channel to visualize the fatty acylation of STAT3 and was stained with Coomassie Brilliant Blue (B7920, Sigma) to check for protein loading. Relative FL/Protein quantification was done by ImageJ.

Synthesis of methyl 2-bromohexadecanoate (MY-D-2). To a solution of 2-bromohexadecanoic acid (2 g, 5.964 mmol) in dry methanol (20 mL), chlorotrimethylsilane (2.44 mL, 19.09 mmol) was added dropwise at room temperature. After stirring overnight at room temperature, the solvent was removed in vacuo. The residue was dissolved in dichoromethane (DCM, 50 mL) and washed with saturated $NaHCO_3$, water, and brine. After drying with sodium sulfate, the organic layer was concentrated. The crude was purified by column (Hexane:Ethyl Acetate=5:1) to afford methyl 2-bromohexadeconate (MY-D-2) as white solid (2.061 g, 98.3%). $^1$H NMR (500 MHz, $C_2D_6OS$) δ 4.52 (dd, J=7.8, 6.6 Hz, 1H), 3.70 (s, 3H), 2.05-1.75 (m, 2H), 1.33-1.18 (m, 24H), 0.84 (t, 3H). $^{13}$C NMR (126 MHz, $C_2D_6OS$) δ 169.85, 52.72, 46.49, 34.31, 31.29, 29.03, 29.02, 29.01, 29.00, 28.83, 28.72, 28.70, 28.18, 26.52, 22.08, 13.92.

Synthesis of 2-bromo-N-phenylhexadecanamide (MY-D-3). To a solution of 2-bromohexadeanoic acid (1 g, 2.863 mmol) in DCM (2 mL) and toluene (10 mL), oxalyl chloride (0.39 mL, 4.580 mmol) was added dropwise at room temperature. To the mixture, one drop of DMF was added. After 2 hours of stirring at room temperature, the solvents were removed, and the residue was co-evaporated with toluene two times (2×3 mL). The residue was re-dissolved in DCM (15 mL). To the mixture, TEA (0.4 mL, 2.862 mmol) and aniline (0.26 mL, 2.862 mmol) were added. The mixture was stirred at room temperature for 3 hours. Then, it was washed by 0.1 N HCl (5 mL), and the collected organic layer was further washed by water and brine. After drying with sodium sulfate and evaporating, the crude residue was purified by column (hexane:ethyl acetate=2:1) to afford 2-bromo-N-pehnylhexxadecanamide (MY-D-3) as a white solid (0.926 g, 79%). $^1$H NMR (500 MHz, $C_2D_6OS$) δ 10.31 (s, 1H), 7.62-7.56 (m, 2H), 7.35-7.29 (m, 2H), 7.13-7.05 (m, 1H), 4.53 (t, J=7.4 Hz, 1H), 2.11-1.82 (m, 2H), 1.34-1.18 (m, 24H), 0.85 (t, J=6.9 Hz, 3H). $^{13}$CNMR (126 MHz, $C_2D_6OS$) δ 166.95, 138.50, 128.87, 123.87, 119.30, 49.79, 34.26, 31.29, 29.04, 29.02, 29.01, 29.00, 28.93, 28.85, 28.74, 28.71, 28.20, 26.80, 22.10, 13.96. LCMS (ESI) calcd. for $[M+H]^+$ $C_{22}H_{37}BrNO$ 410.20, obsd. 410.26.

Synthesis of S-(2-acetamidoethyl) 2-bromohexadecanethioate (MY-D-4). To a solution of 2-bromohexadecanoic acid (200 mg, 0.596 mmol) in DCM (10 mL), N-acetylcysteamine (64.6 mg, 0.542 mmol), N-(3-dimethylaminopropyl)-N'-ethylcarbodiimide hydrochloride (EDC, 124.4 mg, 0.650 mmol) and (4-dimethylamino)pyridine (66.2 mg, 0.542 mmol) were added. After stirring at room temperature for 12 hours, the mixture was washed with water, 0.5 N HCl, and brine. After drying with sodium sulfate and concentrating in vacuo, the crude was purified by column (hexane:ethyl acetate=3:1) to afford S-(2-acetamidoethyl) 2-bromohexadecanethioate as white solid (230 mg, 88.6%). $^1$H NMR (500 MHz, $C_2D_6OS$) δ 8.05 (t, J=5.8 Hz, 1H), 4.79 (dd, J=7.8, 6.2 Hz, 1H), 3.26-3.06 (m, 2H), 2.96 (td, J=6.7, 2.7 Hz, 2H), 2.04-1.82 (m, 2H), 1.78 (s, 3H), 1.40-1.17 (m, 24H), 0.84 (t, 3H). $^{13}$C NMR (126 MHz, $C_2D_6OS$) δ 195.56, 169.29, 54.39, 37.80, 34.61, 31.30, 29.05, 29.03, 29.01, 29.00, 28.95, 28.91, 28.84, 28.72, 28.70, 28.22, 26.47, 22.50, 22.10, 13.96. LCMS (ESI) calcd. for $[M+H]+C_{20}H_{39}BrNO2_s$ 436.18, obsd. 436.22.

While there have been shown and described what are at present considered the preferred embodiments of the invention, those skilled in the art may make various changes and modifications which remain within the scope of the invention defined by the appended claims.

What is claimed is:

1. A method for screening candidate compounds as inhibitors of acyl transferase activity, the method comprising:
   (i) preparing a reaction mixture comprising: (a) an acyl transferase enzyme, (b) a peptide substrate bound to a fluorophore, wherein the substrate comprises the amino acid sequence ISKEEKTPGCVKIKK (SEQ ID NO: 1), wherein up to five amino acids in the sequence other than cysteine (C) may be replaced with other amino acids, (c) an acyl-CoA, (d) a detergent comprising micelles, and (e) a candidate compound; wherein the acyl transferase enzyme mediates acylation on said peptide substrate to result in association of the peptide with micelles of the detergent with resultant increase in fluorescence polarization;
   (ii) measuring the fluorescent signal of the reaction mixture;
   wherein a decrease in fluorescence polarization of the reaction mixture compared to fluorescence polarization of a control reaction not containing said candidate compound indicates that the candidate compound inhibits acyl transferase.

2. The method of claim 1, wherein said acyl transferase enzyme is a palmitoyl transferase, and said acyl-CoA is palmitoyl-CoA.

3. The method of claim 1, wherein the acyl transferase enzyme is a ZDHHC acyltransferase.

4. The method of claim 1, wherein the acyl transferase enzyme primarily uses palmitoyl-CoA as an acyl donor.

5. The method of claim 1, wherein the peptide substrate is a peptide fragment of a Ras family protein.

6. The method of claim 1, wherein the fluorophore comprises a carboxyfluorescein (FAM) group.

7. The method of claim 1, wherein the detergent comprises n-dodecyl β-D-maltoside (DDM).

8. The method of claim 1, wherein the detergent is present in the first reaction mixture in a concentration of 0.01-0.2 v/v %.

9. The method of claim 1, wherein the detergent is present in the first reaction mixture in a concentration of 0.1 v/v %.

* * * * *

SEQUENCE LISTING

<160> NUMBER OF SEQ ID NOS: 1

<210> SEQ ID NO 1
<211> LENGTH: 15

```
<212> TYPE: PRT
<213> ORGANISM: Artificial Sequence
<220> FEATURE:
<223> OTHER INFORMATION: Peptide sequence

<400> SEQUENCE: 1

Ile Ser Lys Glu Glu Lys Thr Pro Gly Cys Val Lys Ile Lys Lys
1               5                   10                  15
```